| United States Patent [19] | [11] | 4,294,844 |
|---|---|---|
| Harris | [45] | Oct. 13, 1981 |

[54] USE OF 4,5-DIHYDRO-2-LOWER ALKOXYCARBONYLAMINO-4-PHENYL IMIDAZOLES AND SUBSTITUTED PHENYL DERIVATIVES THEREOF AS ANTI-HYPERTENSIVE AGENTS

[75] Inventor: George S. Harris, Palo Alto, Calif.

[73] Assignee: Syntex (U.S.A.) Inc., Palo Alto, Calif.

[21] Appl. No.: 44,900

[22] Filed: Jun. 4, 1979

[51] Int. Cl.³ ............................................. A61K 31/415
[52] U.S. Cl. ................................................ 424/273 R
[58] Field of Search .................................... 424/273 R

[56] References Cited

U.S. PATENT DOCUMENTS

| 4,088,771 | 5/1978 | Roszkowski | 424/273 R |
| 4,129,661 | 12/1978 | Roszkowski | 424/273 R |

OTHER PUBLICATIONS

J. Med. Chem., vol. 16, No. 8, 1973, p. 901.

*Primary Examiner*—Anna P. Fagelson
*Attorney, Agent, or Firm*—Tom M. Moran; Alan M. Krubiner; Kate H. Murashige

[57] ABSTRACT

4,5-Dihydro-2-lower alkoxycarbonylamino-4-phenyl imidazoles and substituted phenyl derivatives thereof lower the blood pressure in a human being when administered at low doses.

5 Claims, No Drawings

USE OF 4,5-DIHYDRO-2-LOWER ALKOXYCARBONYLAMINO-4-PHENYL IMIDAZOLES AND SUBSTITUTED PHENYL DERIVATIVES THEREOF AS ANTI-HYPERTENSIVE AGENTS

BACKGROUND OF THE INVENTION

1. The Prior Art

It is known that compounds useful in the method of this invention are useful as central nervous system (CNS) agents are shown in U.S. Pat. No. 4,129,661, issued Dec. 12, 1978. Related compounds which are substituted with an alkyl group at the 1-position of the imidazoline ring are also known to be active as CNS agents. See for example U.S. Pat. No. 4,088,771 issued May 9, 1978. It is further known that certain 2-amino-4-aryl-2-imidazolines are useful as anti-hypertensive agents. See Journal of Medical Chemistry, Vol. 16, No. 8, page 901 (1973).

FURTHER DISCUSSION OF THE INVENTION

This invention is a method for lowering blood pressure in a hypertensive human being by administering a compound (or a pharmaceutically acceptable salt thereof) of the formula

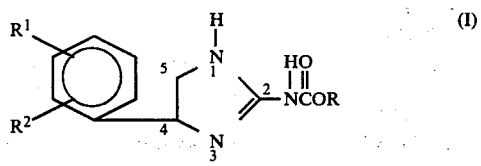

wherein

R is lower alkyl;

$R^1$ is hydrogen, hydroxy, lower alkyl, lower alkoxy, fluoro, chloro, bromo, iodo or trifluoro methyl; and $R^2$ is hydrogen or a substituent identical to $R^1$, and wherein $R^1$ and $R^2$ can be at any position on the phenyl ring or $R^1$ and $R^2$ together form methylenedioxy and are at adjacent carbon atoms on the phenyl ring.

Compounds of formula (I) wherein R is methyl and $R^1$ and $R^2$ are each chloro are preferred, while the 2,6-dichloro compound is particularly preferred.

The method of this invention comprises administering a effective amount of a compound of Formula (I) to a hypertensive human being, that is, one who has high blood pressure. A therapeutically effective amount is a quantity sufficient to lower the blood pressure in the human being treated, i.e. enough to result in a hypotensive effect. Thus, the compounds employed in the method of this invention are anti-hypertensive agents. In general, the dosage depends upon the particular subject and the severity of the order being treated and can vary within wide limits such as, for example, between 0.01 and 10 milligrams per kilogram of body weight per day, preferably less than 1.0 mg/kg.

The compounds can be administered orally, rectally, sublingually or parenterally (for example, by intravenous, intraperitoneal or intramuscular injection). Where the compounds are adminstered parenterally, they will be adminstered in liquid dosage forms, whereas when administered orally or rectally, they can be administered in either solid or liquid forms. Typically, a dosage form comprises a compound in a pharmaceutically acceptable carrier, preferably formulated in unit dosage form to facilitate the simple administration of a precise dosage. The dosage form can optionally contain other compatible medicaments, preservatives, emulsifying agents, wetting agents and/or buffering agents. Liquid dosage forms include for example, solutions, suspensions, emulsions, syrups, elixirs, aerosols, etc. Liquid carriers include for example water, saline solution, and other suitable non-reactive liquid carriers. Solid dosage forms include, for example, tablets, powders, capsules, pills, etc. Suitable solid carriers include, for example, pharmaceutical grades of starch, lactose, sodium saccharine, sodium bisulfate, polyethylene glycol, polysorbate, stearic acid, diglycol stearate, etc.

The preferred unit dosage is generally in the form of a pill which can be swallowed. This can be a solid tablet or a gelatin capsule enclosing a powder or liquid. Generally, each pill will contain about 5-250 mg of active ingredient, preferably about 10-100 mg.

The compounds which are useful in the method of this invention are set forth in U.S. Pat. No. 4,129,661, issued Dec. 12, 1978. That patent is incorporated herein by reference.

The following examples are given to more fully illustrate the invention but is not meant to limit the scope of the claims attached hereto.

EXAMPLE 1

Three and one-half (3.5) grams (g) of the dihydrochloride salt of β-amino-β-(2,6-dichlorophenyl)ethylamine is added to a suitable reaction vessel containing 30 milliliters (ml) of saturated sodium bicarbonate. The resulting mixture is stirred, diluted with 50 mls of isopropanol and a solution of 2.8 g of a mixture of 1-mono-amd 1,3-bis(methoxycarbonyl)-S-methylisothiourea in 50 ml of chloroform is added. Stirring is continued for six days and the solvents are removed under vacuum. The residue is stirred with 70 ml of 2% hydrochloric acid for 30 minutes and the acidic aqueous solution is washed several times with ether, once with toluene and is then treated with excess of saturated sodium bicarbonate. The resulting precipitate is collected by filtration, stirred with water, collected again and dried at 55° under vacuum affording 2.25 g of 4,5-dihydro-4-(2,6-dichlorophenyl)-2-methoxycarbonylaminoimidazole, melting point (mp) 227°-229° C. A small sample is further purified by recrystallization from toluene to give 4,5-dihydro-4-(2,6-dichlorophenyl)-2-methoxycarbonylaminoimidazole, mp 230°-231° C.

EXAMPLE 2

Each of two healthy human volunteers was given a gelatin capsule containing 10 milligrams (mg) 4,5-dihydro-4-(2,6-dichlorophenyl)-2-methoxycarbonylaminoimidazole. A hypotensive effect was seen within three hours in each volunteer.

EXAMPLE 3

The procedure of Example 2 was repeated using a dose of 25 mg of the same compound per volunteer. A hypotensive effect was also seen at this dose.

EXAMPLE 4

Each of four healthy human volunteers was given a gelatin capsule containing 50 mg of 4,5-dihydro-5-(2,6-dichlorophenyl)-2-methoxycarbonylaminoimidazole. A hypotensive effect was seen in each volunteer within three hours.

EXAMPLE 5

This example sets forth the process for preparing a representative capsule formulations for 4,5-dihydro-4-(2,6-dichlorophenyl)-2-methoxycarbonylaminoimidazole (Compound A here and in Examples 6 and 7) useful in the method of this invention

|   | Ingredient | Amount |
|---|---|---|
| A. | Compound A | 10 mg |
|   | Lactose BP | 75 mg |
|   | Magnesium Sterate | 0.75 mg |
| B. | Compound A | 10 mg |
|   | Lactose BP | 250 mg |
|   | Magnesium Stearate | 0.75 mg |
| C. | Compound A | 20 mg |
|   | StaRx-1500(prehydrolyzed) starch) | 75 mg |
|   | Magnesium Stearate | 0.75 mg |
| D. | Compound A | 20 mg |
|   | StaRx-1500 | 250 mg |
|   | Magnesium Stearate | 0.75 mg |

In each of formulations A-D, the ingredients are mixed thoroughly according to methods well known in the art, and capsules are filled with the mixture.

EXAMPLE 6

The following formulations are prepared by the wet granulation method using techniques known in the pharmaceutical art as Exemplified by "Remington's Pharmaceutical Sciences," 15th ed., Mack Publishing Company, Easton, PA, pp 1583–1586, 1965 to prepare tablets, each containing 10 mg of compound A.

|   | Ingredient | Amount |
|---|---|---|
| A. | Compound A | 10% |
|   | Lactose | 68% |
|   | Cornstarch | 10.5% |
|   | Sodium Carboxymethyl Starch | 4% |
|   | Cornstarch (as paste) | 5% |
|   | Talc | 2% |
|   | Magnesium Stearate | 0.5% |
| B. | Compound A | 10% |
|   | Lactose | 68% |
|   | Cornstarch | 15.1% |
|   | Sodium Carboxymethyl Starch | 4% |
|   | Polyvynlpyrollidone BPC (as solution) | 0.4% |
|   | Talc | 2% |
|   | Magnesium Stearate | 0.5% |

The following formulation is prepared by thoroughly mixing all of the ingredients and tabletting by the direct compression method as discussed in Remington's, supra, p 1587 to prpare a tablet containing 25 mg of Compound A.

| Ingredient | Amount |
|---|---|
| Compound A | 25% |
| Dibasic Calcium Phosphate Dihydrate | 72% |
| Sodium Carboxymethyl Starch | 2% |
| Magnesium Stearate | 1% |

The subject matter claimed is:

1. A method for lowering the blood pressure in a hypertensive human being which comprises administering to said human being a therapeutically effective hypotensive amount of a compound chosen from those represented by the formula

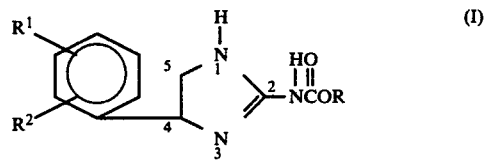

wherein
R is lower alkyl;
$R^1$ is hydrogen, lower alkyl, hydroxy, lower alkoxy, fluoro, chloro, bromo, iodo or trifluoro methyl; and
$R^2$ is hydrogen or is a substituent which is identical to the $R^1$ substituent, and wherein $R^1$ and $R^2$ can be at any position on the phenyl ring or $R^1$ and $R^2$ together form methylenedioxy and are at adjacent carbon atoms on the phenyl ring, and the pharmaceutical salts thereof.

2. The method of claim 1 wherein the amount administered is 0.01 to 10 mg of said compound per kg weight of said human being.

3. The method of claim 1 wherein said compound is represented by Formula (I) wherein $R^1$ and $R^2$ are both chloro and R is methyl.

4. The method of claim 3 wherein said compound is 4,5-dihydro-2-methoxycarbonylamino-4-(2,6-dichlorophenyl)imidazole.

5. The method of claim 3 wherein the amount administered is 0.01 to 10 mg of said compound per kg weight of said human being.

* * * * *